United States Patent
Maassen et al.

(10) Patent No.: US 7,943,047 B2
(45) Date of Patent: May 17, 2011

(54) PROCESS FOR THE TREATMENT OF WASTEWATER FROM ALDOLIZATION PROCESSES

(75) Inventors: Siegmar Maassen, Ludwigshafen (DE); Roland Krokoszinski, Weisenheim A.berg (DE); Detlef Kratz, Singapore (SG)

(73) Assignee: BASF SE, Ludwigshafen (DE)

( * ) Notice: Subject to any disclaimer, the term of this patent is extended or adjusted under 35 U.S.C. 154(b) by 501 days.

(21) Appl. No.: 12/088,777

(22) PCT Filed: Sep. 25, 2006

(86) PCT No.: PCT/EP2006/066669
§ 371 (c)(1),
(2), (4) Date: Mar. 31, 2008

(87) PCT Pub. No.: WO2007/036500
PCT Pub. Date: Apr. 5, 2007

(65) Prior Publication Data
US 2008/0251458 A1    Oct. 16, 2008

(30) Foreign Application Priority Data
Sep. 30, 2005    (DE) .................. 10 2005 047 460

(51) Int. Cl.
*B01D 11/04*    (2006.01)
*C07C 45/80*    (2006.01)
(52) U.S. Cl. ............ 210/639; 203/10; 203/39; 210/774; 210/805; 210/806; 210/908; 568/463; 568/492
(58) Field of Classification Search .............. 203/10, 203/28, 39; 210/634, 638, 639, 774, 805, 210/806, 908, 909; 568/463, 464, 492, 878, 880
See application file for complete search history.

(56) References Cited

U.S. PATENT DOCUMENTS

| | | | | |
|---|---|---|---|---|
| 1,839,819 | A * | 1/1932 | Whitehead | 8/440 |
| 3,359,335 | A * | 12/1967 | Roming, Jr. | 568/919 |
| 4,064,079 | A * | 12/1977 | Sidebotham et al. | 521/48 |
| 4,518,502 | A * | 5/1985 | Burns et al. | 210/634 |
| 5,336,811 | A * | 8/1994 | Fried | 568/436 |
| 6,139,747 | A | 10/2000 | Rotzheim et al. | |
| 6,340,778 | B1 * | 1/2002 | Bueschken et al. | 568/463 |
| 6,358,419 | B1 | 3/2002 | Rotzheim et al. | |
| 6,433,230 | B1 * | 8/2002 | Bueschken et al. | 568/388 |
| 2004/0262238 | A1 | 12/2004 | Munnig et al. | |
| 2005/0115901 | A1 | 6/2005 | Heuser et al. | |

FOREIGN PATENT DOCUMENTS
EP    0631988    1/1995
(Continued)

*Primary Examiner* — Joseph W Drodge
(74) *Attorney, Agent, or Firm* — Connolly Bove Lodge & Hutz LLP

(57) ABSTRACT

Process for the treatment of wastewater from an aldolization process which is contaminated with water-soluble and/or dispersed organic impurities by means of single-stage or multistage extraction with an organic liquid of the aldolization process wastewater which has been set to a pH of from 0 to 6, in which an organic liquid obtained by stripping of the acidified aldolization process wastewater or of the acidified and extracted aldolization process wastewater, condensation of the stripped compounds and phase separation of the condensate is used as extractant for the extraction of organic impurities from the acidified aldolization process wastewater and wastewater having a lower content of organic impurities than the aldolization process wastewater fed to the extraction is taken off from the stripping apparatus.

11 Claims, 1 Drawing Sheet

FOREIGN PATENT DOCUMENTS

Figure 1:
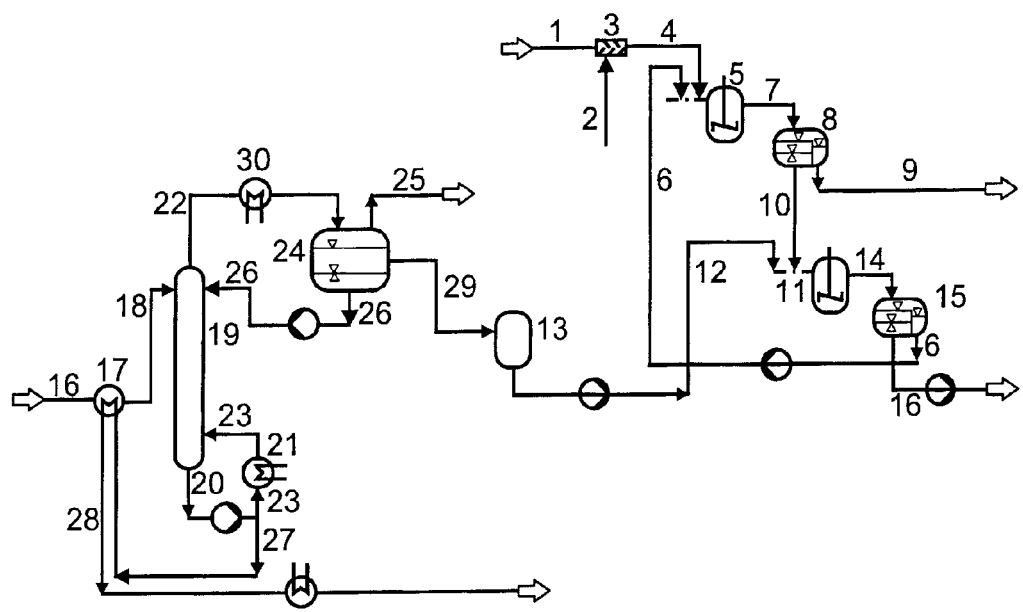

| | | |
|---|---|---|
| EP | 0926100 | 6/1999 |
| EP | 1496043 | 1/2005 |
| GB | 960936 | 6/1964 |
| GB | 1309555 | 3/1973 |
| WO | 2003070639 | 8/2003 |

* cited by examiner

PROCESS FOR THE TREATMENT OF WASTEWATER FROM ALDOLIZATION PROCESSES

CROSS REFERENCE TO RELATED APPLICATIONS

This application is a National Phase of International Application No. PCT/EP2006/066669 filed on Sep. 25, 2006, which claims priority to Application No. 102005047460.8 filed in Germany on Sep. 30, 2005; the entire contents of all are hereby incorporated by reference.

The present invention relates to a process for the treatment of wastewater from an aldolization process which is contaminated with water-soluble organic impurities by means of single-stage or multistage extraction with an organic liquid of the aldolization process wastewater which has been set to a pH of from 0 to 6.

Base-catalyzed aldolization reactions, for example aldol additions and aldol condensations, have attained considerable importance in the industrial preparation of alcohols. Merely by way of example, mention may be made of the preparation of neopentyl glycol in which formaldehyde is added onto isobutyraldehyde to form 2,2-dimethyl-3-hydroxypropanal in a first step of the synthesis. The preparation of the plasticizer alcohols 2-ethylhexanol and 2-propylheptanol is carried out on a far larger scale in a process in which two molecules of n-butyraldehyde or n-valeraldehyde are condensed in an aldol condensation with elimination of water to form the unsaturated aldehyde 2-ethylhexenal or 2-propylheptenal in the first step of the synthesis and this unsaturated aldehyde is subsequently hydrogenated to give the respective plasticizer alcohol (cf. Weissermel, Arpe; Industrielle Organische Chemie; 4th Edition, pp. 150-152, 231-232, Wiley-VCH, Weinheim 1994).

The base-catalyzed aldol addition of aldehydes to form β-hydroxyaldehyde adducts or the aldol condensation of two aldehydes to form the respective α,β-unsaturated aldehydes, also referred to as enalization, or the aldol condensation of aldehydes with ketones which is in each case either catalyzed by means of an aqueous base, e.g. sodium hydroxide, or requires a hydrolysis step or an extraction with water to remove the base from the product during the work-up results in considerable amounts of wastewater which is heavily contaminated with water-soluble organic compounds and organic compounds dispersed in water. Although these organic impurities in the wastewater are generally biodegradable, the biological degradation of these impurities, e.g. in a water treatment plant, has a relatively high oxygen demand. The magnitude of this oxygen demand is estimated by means of the easily determined COD value (COD=chemical oxygen demand) which is determined by oxidizing a water sample with an excess of dichromate solution and backtitrating the excess dichromate (cf. Deutsche Einheitsverfahren zur Wasser-, Abwasser- und Schlammuntersuchung, DIN 38406, part 44, May 1992 edition). As a result of the high oxygen demand for degradation of aldolization process wastewater in a water treatment plant, a correspondingly high oxygen input into the wastewater has to be ensured, which in turn requires a high energy consumption for the increased introduction of air into the wastewater, possibly associated with an expansion of the capacity of the water treatment plant. If this is not possible, there is a risk of the COD of the wastewater going in to the main outfall from the water treatment plant exceeding the legal limits or the aerobic degradation of the organic substances comprised in the wastewater failing because of lack of oxygen and undesirable anaerobic decomposition of the wastewater commencing, which is generally referred to as overturning of the water treatment plant.

To avoid such disadvantageous consequences in the high costs associated with the treatment of such wastewater, highly polluted wastewater from aldolization plants is advantageously subjected to pretreatment to reduce the COD.

Such pretreatment of an aldolization process wastewater is described by way of example for the wastewater formed in the aldol condensation of n-butyraldehyde to give 2-ethylhexenal in EP-A 631 988. Here, the aldolization process wastewater is, if appropriate after mixing with other washing water from 2-ethylhexanol production, acidified to a pH of from 0 to 6, the organic phase formed is separated off and the aqueous phase is extracted with a $C_8$-$C_{16}$-monoalcohol, in this specific case with 2-ethylhexanol. The wastewater which has been treated in this way is passed to the water treatment plant while the organic extract comprising the organic impurities which have been separated off, essentially by-products from 2-ethylhexanol production, is distilled to recover the extractant, in the present case 2-ethylhexanol.

A disadvantage of the method described in EP-A 631 988 is that the high-boiler constituents which accumulate in the bottom of the distillation column in the recovery of the extractant by distillation interfere in its recovery and lead to a continual temperature increase in the bottom of the distillation column. High temperatures in turn cause further condensation of the high-boiling compounds and finally deposits in the distillation column. In order to prevent the temperatures at the bottom from rising above a particular level, part of the 2-ethylhexanol therefore has to remain in the bottom of the column. This 2-ethylhexanol is then lost together with the high-boiling constituents in the disposal of the residues, so that fresh 2-ethylhexanol always has to be added to the 2-ethylhexanol recirculated to the extraction.

To avoid the indicated disadvantages of the process of EP-A 631 988, EP-A 926 100 proposes a process in which the various wastewater streams from 2-ethylhexenal and 2-ethylhexanol production are, either individually or after having been conveyed, set to a pH of from 0 to 6 and subsequently passed through a coalescing filter to separate off the organic phase. The aqueous phase obtained in this way, which has been freed of the major part of the organic impurities, is subsequently extracted with a $C_8$-$C_{16}$-monoalcohol, in this specific case 2-ethylhexanol, to separate off organic constituents which are still dissolved or dispersed therein. According to EP-A 926 100, this procedure reduces the proportion of high-boiling impurities which go into the organic extract to such an extent that the losses of extractant, e.g. 2-ethylhexanol, in the bottom of the column in the subsequent recovery of the extractant by distillation are reduced. EP-A 926 100 comprises no information on the extent of the losses of extractant, but losses of 2-ethylhexanol cannot be avoided in the process of EP-A 926 100 either.

It was therefore an object of the present invention to discover an improved process for the treatment of wastewater from an aldolization process which is contaminated with water-soluble organic impurities, which process makes it possible, in an economical and ecologically efficient manner, to reduce the chemical oxygen demand of the aldolization process wastewater to such an extent that it can be degraded without problems in a water treatment plant. In particular, the use of an expensive extractant and the process engineering outlay to achieve highly loss-free recovery of the extractant by distillation should be avoided. In addition, the process should be suitable for continuous operation.

We have accordingly found a process for the treatment of wastewater from an aldolization process which is contaminated with water-soluble and/or dispersed organic impurities by means of single-stage or multistage extraction with an organic liquid of the aldolization process wastewater which has been set to a pH of from 0 to 6, wherein an organic liquid obtained by stripping of the acidified aldolization process wastewater or of the acidified and extracted aldolization process wastewater, condensation of the stripped compounds and phase separation of the condensate is used as extractant for the extraction of organic impurities from the acidified aldolization process wastewater and wastewater having a lower content of organic impurities than the aldolization process wastewater fed to the extraction is taken off from the stripping apparatus.

The process of the invention differs fundamentally from the processes of EP-A 631 988 and EP-A 926 100 in that the extractant used is not a product of value, e.g. 2-ethylhexanol, but instead the low-boiling, organic first fraction from, for example, the distillation of 2-ethylhexanol, n-butanol, isobutanol, pentanol and/or 2-propylheptanol, which is usually incinerated anyway;

recovery of the extractant from the organic wastewater extract is therefore not necessary for economic reasons;

the extracted wastewater is easily freed of extractant still comprised therein by stripping and its COD is reduced further in this way, and the organic low boiler mixture obtained in the stripping step is reused as extractant for the aldolization process wastewater.

An energy-intensive work-up of the organic wastewater extract by distillation, which is associated with losses of extractant, does not take place in the process of the invention.

The wastewater from aldolization processes to be treated according to the invention is formed, for example, in the aldol condensation of aldehydes to form the corresponding α,β-unsaturated aldehydes, for example the condensation of n-butyraldehyde to form 2-ethylhexenal or the condensation of n-valeraldehyde to form 2-propylheptenal, in the presence of aqueous alkali metal hydroxide solution as catalyst. After leaving the condensation reactor, the aqueous-organic reaction product mixture is subjected to a phase separation in which an organic phase consisting essentially of the desired aldol condensation product and an aqueous phase are formed. While the organic phase is processed further to obtain the desired end products, for example in the case of the production of 2-ethylhexenal by hydrogenation to give 2-ethylhexanol or in the case of the production of 2-propylheptenal by hydrogenation to give 2-propylheptanol, the aqueous phase which is contaminated with organic impurities generally has to be pretreated before it is introduced into the water treatment plant. Depending on their water solubility, the organic impurities present in the aqueous phase can be completely or partly present in solution and/or in the form of finely dispersed, microscopically small droplets or particles.

As by-products which can be formed in the aldol condensation and can be present partly as a solution or dispersion in the aqueous phase and partly as a solution in the organic phase which has been separated off from the aqueous phase and comprising the aldol condensation product, mention may be made by way of example and generically of the groups of compounds in the following, nonexhaustive listing:

isomers of the carbonyl compounds (aldehydes, ketones) used in the aldol condensation, in particular branched aldehydes;

reduced compounds of the carbonyl compounds used, in particular straight-chain and branched alcohols;

lactones having a number of carbon atoms corresponding to the aldehyde used or the aldol condensation product formed;

alcohols which have one more carbon atom than the carbonyl compound used in the aldol condensation and alcohols having twice the number of carbon atoms as the carbonyl compound used;

salts, in particular alkali metal salts, of carboxylic acids having a number of carbon atoms corresponding to the aldehyde used and/or the aldol condensation product and salts of the corresponding hydroxycarboxylic acids formed by alkaline hydrolysis of the lactones;

saturated aldehydes having a number of carbon atoms corresponding to the aldol condensation product formed;

carboxylic esters formed from the abovementioned carboxylic acids and alcohols;

acetals and hemiacetals of the carbonyl compounds mentioned with the alcohols mentioned.

Of course, carbonyl compounds which have been used in the aldol condensation but have not reacted can also be present in the organic phase and aqueous phase of the aldolization product mixture.

Owing to the high alkalinity of the aqueous phase of the aldolization product mixture, the abovementioned salts, in particular, are present therein in dissolved form. Owing to their sometimes long alkyl chains, these salts act as solubilizers for other sparingly soluble by-products and thus increase their content in the aqueous phase, whether in dissolved or dispersed form.

The aldolization process wastewater is therefore brought to a pH generally from 0 to 6, preferably from 1 to 3, before being treated according to the process of the invention. This acidification can be carried out using any strong protic acids, preferably mineral acids such as hydrochloric acid, sulfuric acid, phosphoric acid or nitric acid, particularly preferably sulfuric acid. If desired, wastewater from other processes which is contaminated with organic substances, for example the water which separates off after condensation of the overhead product from the distillation of n-butanol, isobutanol, pentanol, 2-ethylhexanol and/or 2-propylheptanol, can be added for further treatment to the wastewater from the aldolization process before it is acidified. However, preference is given to feeding only the acidified aldolization process wastewater to the extraction. The acidification of the aldolization process wastewater can be carried out in any apparatuses suitable for mixing two liquids, for example in stirred vessels or static mixers, preferably static mixers. The pH of the aldolization process wastewater can be measured, for example, by means of a glass electrode.

After acidification of the aldolization process wastewater, an organic phase can separate out spontaneously from the aqueous phase. It is possible to separate off this organic phase before commencement of the extraction, for example by means of a phase separator, but preference is given to feeding the entire acidified aldolization process wastewater to the extraction.

As extractants in the process of the invention, use can advantageously be made of low-boiling, sparingly water-soluble organic waste materials from various production processes and, preferably, in particular in the steady state of the wastewater treatment process of the invention, the organic liquid which is obtained in the stripping of the acidified and extracted wastewater in a stripping apparatus, e.g. a stripping column, after condensation and phase separation of the gaseous overhead output of the stripping column. The abovementioned low-boiling, sparingly water-soluble organic waste materials from various production processes which are suitable as extractants in the process of the invention can be, for example, the organic low boiler fraction from the distillation of the crude n-butanol obtained after hydrogenation of n-butyraldehyde, the organic low boiler fraction from the distillation of the crude isobutanol obtained after hydrogenation of isobutyraldehyde, the organic low boiler fraction obtained from the distillation of the crude n-pentanol obtained after hydrogenation of n-valeraldehyde, the organic low boiler fraction from the distillation of the crude n-pentanol/isopentanol mixtures obtained after hydrogenation of n-valeraldehyde/isovaleraldehyde mixtures, the organic low boiler fraction from the distillation of the crude 2-ethylhexanol obtained after hydrogenation of 2-ethylhexenal or the organic low boiler fraction from the distillation of the crude 2-propylheptanol obtained after hydrogenation of 2-propylheptenal. Mixtures of two or more, up to all, of the organic low boiler fractions mentioned can also advantageously be utilized as extractants in the process of the invention. These organic low boiler fractions can be obtained by feeding the respective hydrogenation product mixture, i.e. the crude alcohol mixture, into the lower or middle part of a distillation column, taking off a low boiler mixture at the top of the column, condensing it and separating the two-phase, aqueous-organic condensate in a phase separator, with the organic phase obtained being able to be used according to the invention as organic low boiler fraction for the extraction of the acidified aldolization process wastewater, while the alcohol which has been substantially freed of low boilers can be taken off, for example, from the bottom of the distillation column concerned or via a side offtake. Although the low boiler mixtures mentioned are generally equally well-suited to the extraction of the acidified aldolization process wastewater from a technical point of view, it can in a particular case be advantageous because of better availability at the site of the aldolization plant for the extraction of the aldolization process wastewater from the aldolization of n-butyraldehyde to form 2-ethylhexenal to be carried out using the abovementioned low boiler fractions from the distillation of n-butanol, isobutanol and/or ethylhexanol and for the extraction in the case of the aldolization of n-valeraldehyde or mixtures of isomeric valeraldehydes to form 2-propylheptenal or 2-propylheptenal isomer mixtures to be carried out using the abovementioned low boiler fractions from the distillation of n-pentanol, pentanol isomer mixtures and/or 2-propylheptanol, in each case advantageously together with the water-insoluble or sparingly water-soluble organic liquid obtained from the wastewater stripping column.

Of course, other extractants such as $C_5$-$C_{10}$-hydrocarbons, $C_6$-$C_{10}$-alcohols, carboxylic esters, e.g. ethyl acetate, ethers, e.g. diethyl ether, dipropyl ether, diisopropyl ether, dibutyl ether, methyl tert-butyl ether and/or ethyl tert-butyl ether, can also be added to the extractant used according to the invention. In general, such an addition is not necessary for technical reasons, which is why the abovementioned extractants to be used according to the invention are preferably used without addition of other extractants.

In accordance with the origin and geneses of the extractants to be used according to the invention, basically the organic, water-insoluble or sparingly water-soluble liquid obtained from the aldolization process wastewater stripping column, optionally supplemented by addition of one or more of the abovementioned low boiler fractions, the composition of the extractants in terms of the components comprised therein and their proportions can be fairly heterogeneous and can vary greatly during the course of continuous operation of the process, both in respect of the content of individual components and in respect of their proportions in the extractant. The information given below on the composition of the extractant to be used according to the invention is accordingly solely for the purposes of illustration and explanation of the process of the invention and is, in particular, not intended to define the composition of the extractant to be used according to the invention or to restrict it in any way, either in terms of the presence or absence of individual components or in terms of their proportions in the extractant. Thus, the extractant to be used according to the invention can comprise all of the various butanol isomers, but predominantly n-butanol, isobutanol and 2-butanol, in any concentrations, in general in a proportion of from 20 to 50% by weight, or a mixture of isomeric pentanols in any concentration, in general in a proportion of from 20 to 50% by weight, mixtures of $C_5$-$C_{11}$-paraffins, in particular heptane, in proportions of from 0 to 30% by weight, n-butyraldehyde and isobutyraldehyde in proportions of from 0 to 5% by weight and/or n-valeraldehyde and isovaleraldehyde in proportions of from 0 to 5% by weight, 2-ethylhexanol and/or 2-propylheptanol or 2-propylheptanol isomer mixture in proportions of from 0 to 30% by weight.

The extraction of the acidified aldolization process wastewater can be carried out in one or more stages.

The single-stage extraction can be carried out using customary extraction apparatuses, for example mixer-settler apparatuses in various configurations. As mixer for mixing the extractant with the acidified aldolization process wastewater, it is possible to use a static or dynamic inline mixer, a stirring apparatus or a pump. As settler, it is possible to use, for example, gravity separators with or without coalescence-promoting internals, likewise centrifugal separators or coalescence filters and also combinations of these apparatuses. A centrifugal extractor can likewise be used advantageously.

In the single-stage extraction, the acidified aldolization process wastewater is mixed with the extractant in the mixer. The extractant can be added to the wastewater in amounts of at least 0.001 kg per kilogram of wastewater and is generally added in an amount of from 0.01 to 0.2 kg, preferably from 0.05 to 0.1 kg, per kilogram of wastewater. Of course, larger amounts of extractant can also be mixed with the wastewater. The extraction can be carried out at temperatures of generally from 5 to 150° C., preferably from 25 to 60° C., and a pressure of generally from 0.1 to 10 bar, preferably from 0.5 to 1.5 bar and particularly preferably at atmospheric pressure.

The organic extract obtained in this way is generally not worked up further in the process of the invention but is instead utilized, for example, for energy generation, but the organic extract can, if desired, also be hydrogenated and worked up to produce products of value. In such a hydrogenation, the by-products from the aldolization which are comprised in the extract are essentially hydrogenated or hydrogenolyzed to form alcohols. On the other hand, the extracted aqueous phase is subjected to stripping in a distillation apparatus, preferably a distillation column, to achieve a further reduction in the content of organic substances still comprised therein, in particular relatively volatile organic substances. To strip out relatively volatile components, the extracted wastewater is introduced into the upper part of the stripping column and a gaseous stripping medium which is introduced into the lower part of the column or is generated there is conveyed in countercurrent to the downward-flowing aqueous stream. The stripping medium can be an inert gas which is not under the conditions prevailing in the stripping column, e.g. nitrogen; preference is given to using steam as stripping medium in the process of the invention. Stripping can generally be carried out at temperatures of from 50 to 150° C. and a pressure of from 0.1 to 4 bar, preferably from 0.5 to 1.5 bar. The vapor leaving the top of the stripping column is condensed and the condensate is separated into an organic phase and an aqueous phase in a phase separator, while incondensable gases can be disposed of, e.g. via a flare. The aqueous phase which has been separated out in this way can advantageously be recirculated to the upper part of the stripping column, while the organic phase can be passed to the extraction stage and there be used as extractant. As an alternative, the organic phase which has been separated out in this way can also be utilized for energy generation or be worked up by hydrogenation to obtain products of value. The organic phase is preferably used as extractant for the extraction of the acidified aldolization process wastewater, particularly when extractants from other processes, e.g. the above-described low boiler fractions, are not continuously available in sufficient amounts for long-term, continuous operation of the process of the invention. The aldolization process wastewater which has been purified in this way can be taken off from the bottom of the stripping column and, after cooling, passed to the water treatment plant. The heat of the hot purified aldolization process wastewater taken off from the bottom of the stripping column can be utilized for heating the extracted aldolization process wastewater fed to the stripping column from the extraction in a heat exchanger.

If desired, other wastewater contaminated with volatile organic constituents can be fed to the stripping column in addition to the extracted aldolization process wastewater for the purpose of stripping. This can be, for example, wastewater from the distillation of butanol, isobutanol, pentanol, 2-ethylhexanol and/or 2-propylheptanol as is obtained in the distillation of the abovementioned hydrogenated products after condensation and phase separation of the low boiler fraction. This makes it possible to achieve, without any great outlay, an additional reduction in the amount of organic substances with which the water treatment plant has to cope.

To obtain extractants, it can be useful during the start-up phase of the process of the invention to free the acidified aldolization process wastewater of volatile organic substances in the stripping column and to use the organic liquid obtained after condensation and phase separation of the vapor as extractant in the extraction stage of the process of the invention. This mode of operation is generally only of importance during the start-up phase of the process of the invention and generally also only when extractants from other sources, for example the abovementioned low boiler fractions, are unavailable or not available in sufficient amounts.

Otherwise, the recirculation of the organic liquid obtained after condensation and phase separation of the vapor from the stripping column to the extraction stage as extractant can be dispensed with if at any time relatively volatile extractants are readily available in sufficient amounts from other processes, e.g. the abovementioned organic low boiler fractions. In such a case, the organic liquid obtained in this way can be utilized, for example, for energy generation.

Accordingly, a further embodiment of the present invention provides a process for the treatment of wastewater from an aldolization process which is contaminated with water-soluble and/or dispersed organic impurities by means of single-stage or multistage extraction with an organic liquid of the aldolization process wastewater which has been set to a pH of from 0 to 6, wherein the organic low boiler fraction from the distillation of the crude n-butanol obtained after hydrogenation of n-butyraldehyde, the organic low boiler fraction from the distillation of the crude isobutanol obtained after hydrogenation of isobutyraldehyde, the organic low boiler fraction from the distillation of the crude n-pentanol obtained after hydrogenation of n-valeraldehyde, the organic low boiler fraction from the distillation of the crude n-pentanol/isopentanol mixtures obtained after hydrogenation of n-valeraldehyde/isovaleraldehyde mixtures, the organic low boiler fraction from the distillation of the crude 2-ethylhexanol obtained after hydrogenation of 2-ethylhexenal and/or the organic low boiler fraction from the distillation of the crude 2-propylheptanol obtained after hydrogenation of 2-propylheptenal is used as organic liquid for the extraction of organic impurities from the acidified aldolization process wastewater, the volatile organic impurities are stripped from the acidified and extracted aldolization process wastewater in a stripping apparatus and a wastewater having a lower content of organic impurities than the aldolization process wastewater fed to the extraction is taken off from the stripping apparatus.

Particularly if a very low COD of the aldolization process wastewater to be passed to the water treatment plant is required, it can be advantageous to carry out the extraction of the acidified aldolization process wastewater in a multistage, for example two-, three- or four-stage, extraction, with the extractant particularly advantageously being able to be conveyed in countercurrent to the wastewater to be extracted.

The multistage extraction of the acidified aldolization process wastewater can likewise be carried out using the extraction apparatuses as have been indicated for the single-stage extraction. For this purpose, two or more of the extraction apparatuses mentioned are connected in series. However, a multistage extraction can also be achieved by the use of a countercurrent extraction column in the process of the invention. A preferred embodiment of multistage extraction when carrying out the process of the invention is the use of a two-stage mixer-settler cascade with aqueous and organic phases being conveyed in countercurrent. The extraction conditions in respect of pressure, temperature and extractants which can be used correspond to those indicated for the single-stage extraction.

The process principle of an advantageous embodiment of the process of the invention is illustrated below by way of example with the aid of the schematic drawing FIG. 1 without this illustrative exposition implying any restriction in respect of the use and/or configuration of the process of the invention.

The aldolization process wastewater goes via line 1 into the static mixer 3 where it is mixed with a mineral acid, for example sulfuric acid, fed in via line 2 and is brought to the desired pH. The acidified aldolization process wastewater is conveyed via line 4 to the mixer 5, in the present drawing a stirred vessel, which is supplied via line 6 with extractant from the second extraction stage. The aldolization process wastewater/extractant mixture obtained in the mixer 5 is transferred via line 7 to the phase separator 8, in the drawing a gravity phase separator, and separates there into an aqueous phase and an organic phase. The organic phase is disposed of via line 9, for example to energy generation, while the aqueous phase is introduced via line 10 into the second extraction stage comprising the mixer (stirred vessel) 11 and the settler (gravity phase separator) 15 connected thereto via line 14. The mixer 11 receives fresh extractant from the collection vessel 13 via line 12. The extractant which has been separated off in the phase separator is conveyed in countercurrent via line 6 to the first extraction stage with the mixer 5/settler 8, while the acidified and extracted aldolization process wastewater is pumped via lines 16 and 18, after preheating in the heat exchanger 17, into the upper part of the stripping column 19. The stripping column 19 is heated by means of the circulation vaporizer 21 and for this purpose an aldolization process wastewater stream is circulated via line 20, the vaporizer 21 and line 23 to the column. The steam generated by the vaporizer 21 strips the volatile organic impurities from the aldolization process wastewater present in the column 19 and these are discharged from the top of the column 19 via line 22. The vapor comprising steam and stripped organic components is condensed in the condenser 30 and separated into a gas phase, an organic phase and an aqueous phase in the phase separator 24. The incondensable constituents of the vapor are disposed of via line 25, for example to a flare or another incineration apparatus. The aqueous phase is recirculated via line 26 to the upper part of the stripping column 19 and together with aldolization process wastewater fed in via line 18 is stripped in countercurrent by the steam generated by the vaporizer 21. In the steady state of the process, a substream of the stripped aldolization process wastewater taken off from the bottom of the column via line 20 is branched off via line 27, used in the heat exchanger 17 for preheating the aldolization process wastewater coming from the extraction and passed via line 28, if optionally after further cooling, to the water treatment plant.

The organic liquid which has been separated off in the phase separator 24 goes via line 29 to the collection vessel 13 which serves as extractant reservoir. All extractants used in the process of the invention, for example also the low boiler fractions from the distillation of n-butanol, isobutanol and/or 2-ethylhexanol, are combined (not shown) in the collection vessel 13.

If the stripping column 19 is also to be utilized for stripping wastewater from other processes which comprises volatile organic constituents and does not require acidification, this wastewater is advantageously added to the aldolization process wastewater in line 16.

The following examples illustrate the invention.

EXAMPLES

Analysis

The total organic carbon (TOC) in the wastewater was determined in the following examples in accordance with EN 1484-H3 of 1997. The chemical oxygen demand (COD) was determined in accordance with DIN 38409, part 44 (method H44 of the Deutsche Einheitsverfahren zur Wasser-, Abwasser- und Schlammuntersuchung, May 1992).

Example 1

1500 g of wastewater (feed, F, pH 13.6) from the enalization to produce 2-ethylhexenal having a COD of 26 800 mg/l (TOC=7820 mg/l) were brought to a pH of 2 by means of 150 g of concentrated sulfuric acid and subsequently mixed intensively at atmospheric pressure and a temperature of 25° C. with 41 g of a low boiler mixture (solvent, S) at a phase ratio of S:F=0.025 g/g. The solvent mixture had a composition of about 37% by weight of n-butanol, 27% by weight of i-butanol, 15% by weight of n-heptane, 8% by weight and 1% by weight, respectively, of i- and n-butyraldehyde, 7.5% by weight of water and 4.5% by weight of further organic secondary components. After separation of the phases, this extraction procedure was repeated. 1488 g of the resulting extractant wastewater were subjected to a steam distillation at 1012 mbar until the boiling temperature and the condensation temperature of the vapor formed each reached about 100° C. This gave 116 g of two-phase distillate. The organic phase (54 g) comprised 77% by weight of butanols, 18% by weight of water and also butyric acid and butyraldehydes, and the aqueous phase (62 g) comprised 89% by weight of water and 10% by weight of butanols and also a small amount of secondary components.

The treated wastewater obtained in this way had a COD of 3870 mg/l (TOC=1300 mg/l).

Example 2

In the mixer (V=0.001 m$^3$) of a single-stage, continuously operated mixer-settler, 24 kg/h of wastewater (feed, F, pH 13.6) from the enalization to produce 2-ethylhexenal having a COD of 19 600 mg/l (TOC=6900 mg/l) were brought to a pH of 2 by means of 1.34 kg/h of concentrated sulfuric acid and were intensively mixed at atmospheric pressure and a temperature of 40° C. with 1.94 kg/h of the low boiler mixture mentioned in example 1 (solvent, S, phase ratio of S:F=0.056 g/g). The dispersion formed was subsequently separated continuously into two clear phases in a gravity separator (V=0.002 m$^3$). 1160 g of the resulting extracted wastewater were subjected to a steam distillation at about 1013 mbar until the boiling temperature and the condensation temperature of the vapor formed each reached about 100° C.

The treated wastewater obtained in this way had a COD of 2500 mg/l (TOC=800 mg/l).

The invention claimed is:

1. A process for the treatment of alkaline wastewater from an
   aldolization process which is contaminated with water-soluble and/or dispersed organic impurities by means of single-stage or multistage extraction with an organic liquid of the aldolization process wastewater from the preparation of 2-ethylhexenal or 2-propylheptenal
   which has been acidified to a pH of from 0 to 6, wherein an organic liquid obtained by stripping volatile organic impurities from the acidified aldolization process wastewater or of the acidified and extracted aldolization process wastewater, condensation of the stripped compounds and phase separation of the condensate is used as extractant for the extraction of organic impurities from the acidified aldolization process wastewater, and wastewater having a lower content of organic impurities than the aldolization process wastewater fed to the extraction is taken off from the stripping apparatus.

2. The process according to claim 1, wherein the acidified aldolization process wastewater is extracted in a multistage extraction in which the extractant is conveyed in countercurrent relative to the order of the individual extraction stages.

3. The process according to claim 2, wherein the wastewater from an aldolization process comes from the preparation of 2-ethylhexenal.

4. The process according to claim 3, wherein the organic low boiler fraction from the distillation of crude n-butanol, crude isobutanol and/or crude 2-ethylhexanol is additionally used as organic liquid for the extraction of the aldolization process wastewater.

5. The process according to claim 2, wherein the wastewater from an aldolization process comes from the preparation of 2-propylheptenal.

6. The process according to claim 5, wherein the organic low boiler fraction from the distillation of crude n-pentanol, crude mixtures of n-pentanol and isomeric pentanols and/or crude 2-propylheptanol is additionally used as organic liquid for the extraction of the aldolization process wastewater.

7. The process according to claim 1, wherein the wastewater from an aldolization process comes from the preparation of 2-ethylhexenal.

8. The process according to claim 7, wherein the organic low boiler fraction from the distillation of crude n-butanol, crude isobutanol and/or crude 2-ethylhexanol is additionally used as organic liquid for the extraction of the aldolization process wastewater.

9. The process according to claim 1, wherein the wastewater from an aldolization process comes from the preparation of 2-propylheptenal.

10. The process according to claim 9, wherein the organic low boiler fraction from the distillation of crude n-pentanol, crude mixtures of n-pentanol and isomeric pentanols and/or crude 2-propylheptanol is additionally used as organic liquid for the extraction of the aldolization process wastewater.

11. A process for the treatment of alkaline wastewater from an
  aldolization process which is contaminated with water-soluble and/or dispersed organic impurities by means of single-stage or multistage extraction with an organic liquid of the aldolization process wastewater which has been acidified to a pH of from 0 to 6, wherein the organic low boiler fraction from the distillation of the crude n-butanol obtained after hydrogenation of n-butyraldehyde, the organic low boiler fraction from the distillation of the crude isobutanol obtained after hydrogenation of isobutyraldehyde, the organic low boiler fraction from the distillation of the crude n-pentanol obtained after hydrogenation of n-valeraldehyde, the organic low boiler fraction from the distillation of the crude n-pentanol/isopentanol mixtures obtained after hydrogenation of n-valeraldehyde/isovaleraldehyde mixtures, the organic low boiler fraction from the distillation of the crude 2-ethylhexanol obtained after hydrogenation of 2-ethylhexenal and/or the organic low boiler fraction from the distillation of the crude 2-propylheptanol obtained after hydrogenation of 2-propylheptenal is used as organic liquid for the extraction of organic impurities from the acidified aldolization process wastewater, the volatile organic impurities are stripped from the acidified and extracted aldolization process wastewater in a stripping apparatus and a wastewater having a lower content of organic impurities than the aldolization process wastewater fed to the extraction is taken off from the stripping apparatus.

* * * * *